(12) United States Patent
Cai et al.

(10) Patent No.: US 9,974,321 B2
(45) Date of Patent: May 22, 2018

(54) FISH PROTEIN OLIGOPEPTIDE WITH LOW ALLERGENICITY AND SLIGHT FISHINESS AND INDUSTRIAL PREPARATION METHOD AND APPLICATION THEREOF

(71) Applicant: CHINA NATIONAL RESEARCH INSTITUTE OF FOOD AND FERMENTATION INDUSTRIES, Beijing (CN)

(72) Inventors: Muyi Cai, Beijing (CN); Ruizeng Gu, Beijing (CN); Jun Lu, Beijing (CN); Tao Ma, Beijing (CN); Xingchang Pan, Beijing (CN); Zhe Dong, Beijing (CN); Yong Ma, Beijing (CN); Yaguang Xu, Beijing (CN); Yongqing Ma, Beijing (CN); Zhentao Jin, Beijing (CN); Liang Chen, Beijing (CN); Lu Lu, Beijing (CN); Wenying Liu, Beijing (CN); Ying Wei, Beijing (CN); Haixin Zhang, Beijing (CN); Yan Liu, Beijing (CN); Kelu Cao, Beijing (CN); Jing Wang, Beijing (CN); Guoming Li, Beijing (CN); Ming Zhou, Beijing (CN)

(73) Assignee: CHINA NATIONAL RESEARCH INSTITUTE OF FOOD AND FERMENTATION INDUSTRIES, Beijing (CN)

( * ) Notice: Subject to any disclaimer, the term of this patent is extended or adjusted under 35 U.S.C. 154(b) by 0 days. days.

(21) Appl. No.: 15/442,574

(22) Filed: Feb. 24, 2017

(65) Prior Publication Data
US 2017/0164638 A1 Jun. 15, 2017

Related U.S. Application Data

(63) Continuation of application No. PCT/CN2015/092932, filed on Oct. 27, 2015.

(30) Foreign Application Priority Data

Apr. 30, 2015 (CN) .......................... 2015 1 0218914

(51) Int. Cl.
| | |
|---|---|
| *A23J 1/04* | (2006.01) |
| *A23J 3/04* | (2006.01) |
| *A23J 3/34* | (2006.01) |
| *A23L 33/17* | (2016.01) |
| *A23L 17/20* | (2016.01) |
| *C07K 14/46* | (2006.01) |
| *A23L 33/18* | (2016.01) |

(52) U.S. Cl.
CPC . *A23J 1/04* (2013.01); *A23J 3/04* (2013.01); *A23J 3/34* (2013.01); *A23J 3/341* (2013.01); *A23L 17/20* (2016.08); *A23L 33/17* (2016.08); *A23L 33/18* (2016.08); *C07K 14/461* (2013.01); *A23V 2002/00* (2013.01)

(58) Field of Classification Search
CPC . A23J 1/04; C07K 14/46; A23L 33/18; A23V 2200/00
USPC .......................................................... 435/219
See application file for complete search history.

(56) References Cited

FOREIGN PATENT DOCUMENTS

| | | | |
|---|---|---|---|
| CN | 1943365 A | 4/2007 | |
| CN | 101503728 A | * 8/2009 | ............. C12P 21/06 |
| CN | 101731440 A | 6/2010 | |
| CN | 101897380 A | 12/2010 | |
| CN | 102008004 A | 4/2011 | |
| CN | 103333221 A | 10/2013 | |
| CN | 103621765 A | 3/2014 | |
| CN | 104830936 A | 8/2015 | |

OTHER PUBLICATIONS

Ohshima et al. Rapid Detection of Fish Major Allergen Parvalbumin by Surface Plasmon Resonance Biosensor; Journal of Food Science, vol. 69, No. 8 pp. C652-C658. (Year: 2004).*
Li, Yang et al., "Using Response Surface Methodology to Optimize Hydrolysis of Allergic Protein from Mandarin Fish with Papain" Good Science; vol. 33, No. 19; (2012); pp. 199-204.
International Search Report of corresponding International PCT Application No. PCT/CN2015/092932, dated Feb. 3, 2016.
Document No. GB/T 22729-2008, "Oligopeptides Powder of Marine Fish" People Republic of China National Standard, issued on Dec. 31, 2008, partial translation.

* cited by examiner

*Primary Examiner* — Scott Long
*Assistant Examiner* — Paul C Martin
(74) *Attorney, Agent, or Firm* — J.C. Patents

(57) ABSTRACT

Disclosed are a fish protein oligopeptide with low allergenicity and slight fishiness, and industrial preparation method and application thereof. The method comprises the following steps: 1) washing fresh fish flesh and/or fish wastes, crushing, and adding water to obtain a mixture; 2) performing thermal denaturation on the mixture to obtain a denaturized protein solution; 3) centrifuging the denaturized protein solution to obtain a precipitate, and adding water into the precipitate and grinding, to obtain a slurry; 4) adjusting the slurry to pH 6-9, and sequentially adding a neutral protease, a papain and an alkaline protease to conduct enzymolysis, and after enzyme inactivation, to obtain an enzymatic hydrolysate; 5) centrifuging the enzymatic hydrolysate, and performing membrane filtration on centrifuged supernatant, to obtain the fish protein oligopeptide with low allergenicity and slight fishiness. The method completely eliminates the allergenicity and fishiness of fish proteins, and prevents release of bitter components.

7 Claims, No Drawings

FISH PROTEIN OLIGOPEPTIDE WITH LOW ALLERGENICITY AND SLIGHT FISHINESS AND INDUSTRIAL PREPARATION METHOD AND APPLICATION THEREOF

CROSS-REFERENCE TO RELATED APPLICATIONS

This application is a continuation of International Application No. PCT/CN2015/092932, filed on Oct. 27, 2015, which claims the priority benefit of China Patent Application No. 201510218914.X, filed on Apr. 30, 2015. The contents of the above identified applications are incorporated herein by reference in their entireties.

TECHNICAL FIELD

The present invention relates to a fish protein oligopeptide, and particularly to a fish protein oligopeptide with low allergenicity and slight fishiness and industrial preparation method and application thereof.

BACKGROUND

Fish proteins with which fish flesh is enriched have extraordinarily high nutritive value. The fish proteins contain a large amount of nutrients necessary for human body, which are conducive to reducing contents of blood lipids and cholesterol, especially a large amount of DHA, which are able to promote development of a brain, and is an indispensable nutrient for growth of a nervous system. Therefore, more and more people choose to process and eat fish products. However, fishiness of fish products themselves has a huge influence on taste of processed food, and also molecular weights of proteins in the fish flesh are too large to be absorbed by human body. In some processing techniques of prior art, a common approach is to hydrolyze proteins with a large molecular weight in extreme pH and temperature condition, but this will adversely affect properties of the proteins.

More importantly, fish allergy is considered to be one of the most common food allergies since fish proteins contain a large number of allergens, such as parvalbumin, which is proved by IgE antibody to be able to cause more than 95% of people to develop allergy. Heating and chemical treatment are common methods for eliminating allergenicity, but the heating, which denatures the proteins, is unlikely to remove all allergens among the fish proteins, and the chemical treatment, which is mainly to reduce activity of trypsin inhibitors by chemical reagents, will inevitably give rise to food safety issues such as chemical residuals.

The patent publication No. CN102008004A discloses a method for preparation of fish protein powder enriched with fish skin proteins. This method mainly adopts a neutral protease and bromelain to conduct two-step enzymolysis of a fish skin material. Although the enzymolysis can reduce an average molecular weight of final products to below 6000 Da, the method fails to process and detect allergens in the final products, and thus it is not possible to determine whether the method can reduce allergenic activity, and additionally, the method has complicated operation steps.

Li Yang, et al., suggests a method for preparation of fish protein oligopeptide: proteins of mandarinfish flesh is hydrolyzed in a phosphate buffer with a pH value of 8.00 at 40° C. for 4 h using 2940 U/g of papain, reducing the antigenicity of final product of mandarinfish proteins by 58.33%. However, this method again fails to conduct study on allergenicity of parvalbumin, and besides, brings a concern that the enzymolysis product is highly likely to acquire new allergenicity due to exposure of a linear epitope which is originally hidden within a three dimensional protein structure or a hydrophobic region.

SUMMARY

The present invention provides a fish protein oligopeptide with low allergenicity and slight fishiness and industrial preparation method and application thereof, for overcoming technical deficiencies in the prior art that, for example, allergenicity of fish proteins cannot be eliminated completely and taste of produced products is poor and molecular weights of the proteins are too large to be absorbed.

An industrial method for preparation of the fish protein oligopeptide with low allergenicity and slight fishiness provided by the present invention includes the following steps:

1) washing fresh fish flesh and/or fish wastes, crushing, and adding water to obtain a mixture;

2) performing thermal denaturation on the mixture to obtain a denaturized protein solution;

3) centrifuging the denaturized protein solution to obtain a precipitate, and adding water into the precipitate and grinding, to obtain a slurry;

4) adjusting the slurry to pH 6-9, and sequentially adding a neutral protease, a papain and an alkaline protease to conduct enzymolysis, and after enzyme inactivation, to obtain an enzymatic hydrolysate; and 5) centrifuging the enzymatic hydrolysate, and performing membrane filtration on centrifuged supernatant, to obtain the fish protein oligopeptide with low allergenicity and slight fishiness;

wherein prior to the centrifuging the denaturized protein solution, step 3) further includes washing the denaturized protein solution, and the washing the denaturized protein solution comprises:

centrifuging the denaturized protein solution to obtain the precipitate, and washing the precipitate by adding water thereto, wherein a mass to volume ratio of the precipitate and the water is 1:(1-5).

There is no limitation on species of fish used in the present invention, the fish can be deep-sea fish or freshwater fish; and the fish wastes refer to residual materials after removal of fish flesh, for example, fish skin or fish scales. After washing, the washed fish flesh and/or fish wastes may be crushed to 15-20 meshes, in order to further improve subsequent thermal denaturation effect.

Further, in steps 1), a mass to volume ratio of the fish flesh and/or fish wastes and water is 1:(1-5), namely, 1 kg of fish and/or fish wastes are/is mixed with 1-5 L of water to prepare a mixture. During preparation of the mixture, if the water is too little, the mixture has poor flowability, leading to reduced enzymolysis efficiency; and if the water is too much, reaction volume is too large, affecting a subsequent treatment (such as concentration and the like) and increasing cost accordingly. Here, the water may be pure water, distilled water, deionized water and so on. Deionized water is used in the present invention. In addition, in steps 3), a mass to volume ratio of the precipitate and the water is 1:(1-5).

Further, the thermal denaturation includes: heating the mixture to 75-95° C., maintaining this temperature and continuously stirring for 10-60 min. The thermal denaturation is able to damage spatial structure of the fish proteins, thereby reducing allergenicity of the fish proteins, and meanwhile can solve problems of flowability of the mixture being poor and the solution being viscous, thus facilitating proceeding of subsequent enzymolysis.

Further, the denaturized protein solution is centrifuged to obtain a precipitate, water is added to the precipitate and the precipitate is ground to obtain a slurry. During centrifugation, rotation speed is controlled at 2000-8000 r/min and time is controlled to be 10-60 min; since the precipitate formed after the centrifuging is a solid with a large volume, for the sake of enabling subsequent enzymolysis to proceed more thoroughly, water may be further added into the precipitate, and after crushing and beating, to obtain a slurry. The mass to volume ratio of the precipitate and water is controlled at 1:1-5, and the crushing and beating is conducted until the precipitate is about 20-30 meshes.

In addition, in order to improve removal of fishiness and to enhance content of proteins by reducing impurities such as pigments and fats, steps 3), prior to the centrifuging, further includes a step of washing the denaturized protein solution with water. Specifically, the washing the denaturized protein solution includes: centrifuging the denaturized protein solution to obtain the precipitate, washing the precipitate by adding water thereto, a mass to volume ratio of the precipitate and the water is 1:(1-5), wherein during centrifugation, rotation speed is controlled at 2000-8000 r/min and time is controlled to be 10-60 min. This washing step may be repeated 2-3 times.

The inventor has done a considerable amount of researches about how to completely eliminate allergenicity of fish proteins as well as eliminate fishiness of fish products themselves and inhibit generation of bitter substances in enzymolysis products via an enzyme method, without loss of nutrients in fish. It was found that, a majority of proteases are unable to completely eliminate allergenicity of fish proteins and/or to inhibit generation of bitter substances in enzymolysis products. For example, when a neutral protease is used for processing the fish proteins, the allergenicity of fish proteins can be eliminated to a certain extent, allergenicity elimination effect of the fish proteins is less than satisfactory; and when trypsin is used for processing the fish proteins, allergenicity elimination effect of the fish proteins is not obvious, and even content of allergenic parvalbumin as detected increases somewhat. During the research, the inventor surprisingly found that only when a neutral protease, a papain and an alkaline protease are jointly used during enzymolysis, the allergenicity of the fish proteins can be completely eliminated while the generation of bitter substances in the enzymolysis products is inhibited.

In particular, during the enzymolysis of the present invention, an amount of the neutral protease is 10-100 U/g, an amount of the papain is 10-100 U/g, and an amount of the alkaline protease is 10-100 U/g. Moreover, an amount ratio of the neutral protease, the papain and the alkaline protease is 1:(1-3):(1-3). In addition, prior to the enzymolysis, a sodium hydroxide aqueous solution with a mass concentration of 10-20% may be used to adjust pH value to 6-9, and the enzymolysis is conducted at 30° C.-60° C., and time of the enzymolysis is controlled to be 2-6 h. If time of the enzymolysis is too short (<1 h), it is not conducive to protein degradation, and if the time is too long (>3 h), it may result in generation of bitter and astringent substances. The combination of the neutral protease, the papain and the alkaline protease is favorable to full degradation of the fish proteins in order to eliminate the allergenicity thereof while controlling bitter and astringent taste of enzymolysis products, thereby enabling the fish proteins to be further accepted and consumed by a vast number of consumers. The enzymolysis aforementioned is capable of reducing main allergens i.e., parvalbumin, of the fish proteins, by 99% or more, and meanwhile, it is able to moderately hydrolyze the fish proteins, forming small molecular weight peptides (for example, peptides with molecular weights of less than 1000 Da), which is conducive to boosting absorption of the fish proteins by human body.

In the present invention, amounts of the enzymes are based on weight of fish flesh and/or fish wastes, that is, when 1 g of fish flesh and/or fish wastes are/is used, 10-100 U of the neutral protease. Further, the enzyme inactivation is performed at 110-120° C., and time of the enzyme inactivation is controlled to be 8-12 s.

Further, in the centrifuging the enzymatic hydrolysate of steps 5), rotation speed may be controlled at 2000-8000 r/min, and the centrifuging may be conducted via a conventional equipment, such as a tubular centrifuge. In addition, a filtration membrane with a pore diameter of 1-100 nm may be used to perform the membrane filtration, and the pore diameter may be further 1-50 nm (such as ultrafiltration); and during the membrane filtration, absolute pressure thereof may be controlled at 0.2-0.4 MPa, and temperature at 30-80° C. Membrane filtration of the centrifuged supernatant of the enzymatic hydrolysate can further intercept large molecular weight components, so as to remove large-molecular allergenic protein components in the enzymatic hydrolysate.

In the present invention, following the membrane filtration, the resulting filtrate may be decolorized and concentrated. Specifically, the decolorization may be conducted by a conventional decolorizer, for example, an activated carbon powder, a mass ratio of the decolorizer and the filtrate may be (5-10):100, temperature of the decolorization may be controlled at 70-90° C., for example, 80° C., time of the decolorization may be 20-40 min, the decolorization may be conducted under stirring. After the decolorization, the decolorizer may be removed through a conventional method, for example, using a plate and frame filter. Further, filtrate removal of the decolorizer may be concentrated by evaporation, for example, a double-effect falling film evaporator may be used to conduct concentration. During concentration by the evaporation, vapor pressure may be controlled at 0.1±0.02 MPa and evaporation temperature at 40-80° C. After the concentration, volume of the concentrated solution may be reduced to ⅓-½ of the original volume. Further, sterilization and drying may be conducted after the concentration, thus preparing the fish protein oligopeptide powder with low allergenicity and slight fishiness. The drying, for example, may be spray-drying.

The present invention also provides a fish protein oligopeptide with low allergenicity and slight fishiness prepared in accordance with any one of the above preparation methods. In the fish protein oligopeptide with low allergenicity and slight fishiness, mass content of parvalbumin is ≤200 mg/kg. And in the fish protein oligopeptide with low allergenicity and slight fishiness, the mass content of parvalbumin may be reduced by 99% or more, based on the fish proteins.

Further, in the fish protein oligopeptide with low allergenicity and slight fishiness, mass content of peptides with a molecular weight of less than 5000 Da is >85%, mass content of peptides with a molecular weight of less than 1000 Da is >60%. Even further, in the fish protein oligopeptide with low allergenicity and slight fishiness, the mass content of peptides with a molecular weight of less than 5000 Da is >95%, and the mass content of peptides with a molecular weight of less than 1000 Da is >85%.

The present invention further provides an application of the fish protein oligopeptide with low allergenicity and slight fishiness in food or medicines, wherein the food includes, but is not limited to, infant food, sports functional food and health food, where the infant food may include infant milk powder, infant rice flour and so on.

In the method of the present invention, pre-denaturation of the fish proteins in the fish flesh and then enzymolysis using three specific proteases not only eliminate allergenicity of various allergens, but also prevent enzymolysis products from generating new allergenicity, and content of parvalbumin in the fish proteins is reduced by 99% or more; in addition, the method effectively removes fishiness of fish products themselves, and treats fish flesh material into oligopeptides through physical technology, with mass content of peptides with a molecular weight of 1000 Da or less in the oligopeptide reaching 90% or more, thereby guaranteeing absorption and utilization by human body. Furthermore, the method has simple process and is cost saving, and thus is suitable for large-scale production, and fish protein oligopeptide with low allergenicity and slight fishiness, as prepared by the method, has a wide range of applications.

DETAILED DESCRIPTION

In order to make purpose, technical solutions and advantages of the present invention clearer, technical solutions of the present invention will be clearly and completely described in conjunction with the examples of the present invention, and obviously, the described examples are merely part rather than all of examples of the present invention. Based on the examples of the present invention, all other examples obtained by one with ordinary skill in the art without creative efforts shall fall into the protection scope of the present invention.

All proteases used in the present invention were bought from Novozymes Biotechnology Co., Ltd.

Example 1

1. Preparation of Mixture

A commercially available carp was scaled, deboned and eviscerated, and after washing, was crushed to 18 meshes, to obtain 5 kg of minced fish flesh. 15 L of deionized water was added into the minced fish flesh to obtain a mixture.

2. Thermal Denaturation

The mixture was heated to 80° C., maintaining this temperature and continuously stirring for 40 min, to obtain a denaturized protein solution.

3. Preparation of Slurry

The denaturized protein solution was centrifuged for 30 min at rotation speed of 5000 r/min, and after centrifugation, supernatant liquid was discarded, obtaining 4.9 kg of lower-layer solid.

15 L of deionized water was added into the 4.9 kg of lower-layer solid. The resulting mixture was mixed uniformly under stirring, and was centrifuged for 30 min at rotation speed of 4000 r/min to obtain lower-layer solid. The above steps were repeated twice for the obtained lower-layer solid. Finally, 4.85 kg of precipitate was obtained.

15 L of deionized water was added into the 4.85 kg of precipitate, crushing and beating the precipitate to 25 meshes, thereby obtaining a slurry.

4. Enzymolysis

The slurry was adjusted to pH 7 using 20% by weight of sodium hydroxide aqueous solution, and a neutral protease, a papain and an alkaline protease was added into the slurry, wherein amounts of the neutral protease, the papain and the alkaline protease were all about 50 U per gram of fish flesh. Enzymolysis was performed for about 2 h at a temperature of about 50° C., and then temperature was increased to 110° C. to conduct enzyme inactivation for 10 s, thus obtaining an enzymatic hydrolysate.

5. Centrifugation and Membrane Filtration

The enzymatic hydrolysate was centrifuged at a rotation speed of 6000 r/min, and centrifuged supernatant was collected for later use;

An ultrafiltration membrane with a pore diameter of about 50 nm was used for ultrafiltration of the centrifuged supernatant, and during the ultrafiltration, absolute pressure was controlled at about 0.3 MPa and temperature at about 50° C., thus obtaining an ultrafiltrate.

6. Decolorization, Concentration and Sterilization

An activated carbon powder was added into the ultrafiltrate in a mass ratio of the activated carbon powder and the ultrafiltrate was 10:100. Then decolorization was conducted at about 80° C. for about 30 min under stirring, and after the decolorization, the activated carbon powder was removed via a plate and frame filter, to obtain a decolorized solution;

The decolorized solution was concentrated by evaporation to ½ of original volume thereof, where vapor pressure was controlled at about 0.1 MPa and evaporation temperature was controlled at about 60° C. Sterilization and spray-drying were conducted on the concentrated solution, thereby preparing a fish protein oligopeptide with low allergenicity and slight fishiness.

7. Quality Detection and Taste Evaluation

Various allergens in the above prepared fish protein oligopeptide with low allergenicity and slight fishiness were detected with a Fish-Check ELISA Kit form the Bio-check Company, while a mixture of unprocessed fish flesh was used as a control. The results were shown in Table 1.

Molecular weight distribution of each component of the fish protein oligopeptide with low allergenicity and slight fishiness prepared as above was detected using a method described in the national standard (GB/T 22729-2008) for marine fish oligopeptide powder. The results were shown in Table 2.

The fish protein oligopeptide with low allergenicity and slight fishiness prepared as above was dissolved in water, thus obtaining a solution containing 10% by weight of the fish protein oligopeptide with low allergenicity and slight fishiness; an evaluation team of 20 people (half men and half women) was established for evaluating bitterness and fishiness of the solution of the fish protein oligopeptide with low allergenicity and slight fishiness.

The bitterness was evaluated as follows: taking 1 mL of the solution of the fish protein oligopeptide with low allergenicity and slight fishiness, performing gradient dilution on the solution until the bitterness was just discernable, and calculating an average bitterness value of the 20 people by taking dilution multiple as the bitterness value. The results were shown in Table 3.

The fishiness was evaluated by: calculating an average fishiness value of the 20 people, wherein 0—no fishiness; 1—a little fishiness; 2—slight fishiness; 3—fishiness; 4—moderate fishiness; 5—relatively heavy fishiness; 6—heavy fishiness; 7—very heavy fishiness. The results were shown in Table 3.

Example 2

1. Preparation of Mixture

Fishskin waste of a commercially available salmon was collected, and after washing, was crushed to 20 meshes, to obtain 5 kg of minced fish flesh. 10 L of deionized water was added into the minced fish flesh to obtain a mixture

2. Thermal Denaturation

The mixture was heated to 75° C., maintaining this temperature and continuously stirring for 60 min, to obtain a denaturized protein solution.

3. Preparation of Slurry

The denaturized protein solution was centrifuged for 45 min at rotation speed of 3500 r/min, and after centrifugation, supernatant liquid was discarded, obtaining 4.7 kg of lower-layer solid.

10 L of deionized water was added into the 4.7 kg of lower-layer solid. The resulting mixture was mixed uniformly under stirring, and was centrifuged for 20 min at rotation speed of 4000 r/min to obtain lower-layer solid. The above steps were repeated twice for the obtained lower-layer solid. Finally, 4.5 kg of precipitate was obtained.

15 L of deionized water was added into the 4.5 kg of precipitate, crushing and beating the precipitate to 30 meshes, thereby obtaining a slurry.

4. Enzymolysis

The slurry was adjusted to pH 7.5 using 15% by weight of sodium hydroxide aqueous solution, and a neutral protease, a papain and an alkaline protease was added into the slurry, wherein amounts of the neutral protease, the papain and the alkaline protease were all about 70 U per gram of fish waste. Enzymolysis was performed for about 5 h at a temperature of about 30° C., and then temperature was increased to 110° C. to conduct enzyme inactivation for 10 s, thus obtaining an enzymatic hydrolysate.

5. Centrifuging and Membrane Filtration

The enzymatic hydrolysate was centrifuged at a rotation speed of 8000 r/min, and centrifuged supernatant was collected for later use;

An ultrafiltration membrane with a pore diameter of about 20 nm was used for ultrafiltration of the centrifuged supernatant, and during the ultrafiltration, absolute pressure was controlled at about 0.4 MPa and temperature at about 80° C., thus obtaining an ultrafiltrate.

6. Decolorization, Concentration and Sterilization

An activated carbon powder was added into the ultrafiltrate in a mass ratio of the activated carbon powder and the ultrafiltrate was 5:100. Then decolorization was conducted at about 80° C. for about 30 min under stirring, and after the decolorization, the activated carbon powder was removed via a plate and frame filter, to obtain a decolorized solution;

The decolorized solution was concentrated by evaporation to ⅓ of original volume thereof, where vapor pressure was controlled at about 0.1 MPa and evaporation temperature was controlled at about 80° C. Sterilization and spray-drying were conducted on the concentrated solution, thereby preparing a fish protein oligopeptide with low allergenicity and slight fishiness. Quality detection results, molecular weight distribution and taste evaluation results of the fish protein oligopeptide with low allergenicity and fishiness were respectively shown in Table 1 to Table 3.

Example 3

1. Preparation of Mixture

A commercially available carp was scaled and deboned, obtaining fish flesh and viscera. The fish flesh and viscera, after washing, were crushed to 20 meshes, to obtain 5 kg of the fish flesh and viscera. 20 L of deionized water was added into the fish flesh and viscera to obtain a mixture.

2. Thermal Denaturation

The mixture was heated to 90° C., maintaining this temperature and continuously stirring for 20 min, to obtain a denaturized protein solution.

3. Preparation of Slurry

The denaturized protein solution was centrifuged for 35 min at rotation speed of 4500 r/min, and after centrifugation, supernatant liquid was discarded, obtaining 4.6 kg of lower-layer solid.

20 L of deionized water was added into the 4.6 kg of lower-layer solid. The resulting mixture was mixed uniformly under stirring, and was centrifuged for 25 min at rotation speed of 4000 r/min to obtain lower-layer solid. The above steps were repeated twice for the obtained lower-layer solid. Finally, 4.4 kg of precipitate was obtained.

20 L of deionized water was added into the 4.4 kg of precipitate, crushing and beating the precipitate to 30 meshes, thereby obtaining a slurry.

4. Enzymolysis

The slurry was adjusted to pH 8.5 using 10% by weight of sodium hydroxide aqueous solution, and a neutral protease, a papain and an alkaline protease was added into the slurry, wherein amounts of the neutral protease, the papain and the alkaline protease were all about 20 U per gram of fish flesh and fish waste. Enzymolysis was performed for about 3.5 h at a temperature of about 50° C., and then temperature was increased to 110° C. to conduct enzyme inactivation for 10 s, thus obtaining an enzymatic hydrolysate.

5. Centrifuging and Membrane Filtration

The enzymatic hydrolysate was centrifuged at a rotation speed of 7500 r/min, and centrifuged supernatant was collected for later use;

An ultrafiltration membrane with a pore diameter of about 50 nm was used for ultrafiltrate of the centrifuged supernatant, and during the ultrafiltrate, absolute pressure was controlled at about 0.2 MPa and temperature at about 30° C., thus obtaining a ultrafiltrate.

6. Decolorization, Concentration and Sterilization

An activated carbon powder was added into the ultrafiltrate in a mass ratio of the activated carbon powder and the ultrafiltrate was 8:100. Then decolorization was conducted at about 80° C. for about 30 min under stirring, and after the decolorization, the activated carbon powder was removed via a plate and frame filter, to obtain a decolorized solution;

The decolorized solution was concentrated by evaporation to ⅓ of original volume thereof, where vapor pressure was controlled at about 0.1 MPa and evaporation temperature was controlled at about 60° C. Sterilization and spray-drying were conducted on the concentrated solution, thereby preparing a fish protein oligopeptide with low allergenicity and slight fishiness. Quality detection results, molecular weight distribution and taste evaluation results of the fish protein oligopeptide with low allergenicity and fishiness were respectively shown in Table 1 to Table 3.

Comparative Example 1

The slurry prepared in Example 1 was adjusted to about pH 7. A neutral protease was added into the slurry in an amount of about 150 U per gram of fish flesh, to perform enzymolysis at a temperature of about 40° C. for about 2 h. Enzymatic hydrolysate was centrifuged in accordance with the method in Example 1 (without membrane filtration and decolorization), concentrated, and sterilized, thus obtaining a fish protein oligopeptide with low allergenicity and slight fishiness. Quality detection results thereof were shown in Table 1 and Table 3.

Comparative Example 2

The slurry prepared in Example 1 was adjusted to about pH 8. A trypsin was added into the slurry in an amount of about 200 U per gram of fish flesh, to perform enzymolysis at a temperature of about 40° C. for about 2 h. Enzymatic hydrolysate was centrifuged, concentrated and sterilized, in accordance with the method in Example 1 (without membrane filtration and decolorization), thus obtaining a fish protein oligopeptide with low allergenicity and slight fishiness. Quality detection results thereof were shown in Table 1 and Table 3.

Comparative Example 3

The slurry prepared in Example 1 was adjusted to about pH 7. At 55° C., 0.2% of a neutral protease, based on fish material weight, was added into the slurry, to perform enzymolysis for 0.5 h; the temperature was reduced to 45° C. and 0.1% of bromelain, based on the fish material weight, was added to perform enzymolysis for 0.5 h. Enzymatic hydrolysate was centrifuged, decolorized, concentrated and sterilized, in accordance with the method in Example 1, thus obtaining a fish protein oligopeptide with low allergenicity and slight fishiness. Quality detection results thereof were shown in Table 1 and Table 3.

TABLE 1

Quality detection results of the fish protein oligopeptide with low allergenicity and slight fishiness

| Experimental examples | Parvalbumin |
| --- | --- |
| Fish flesh material | $1.37 * 10^5$ mg/kg |
| Example 1 | 121.37 mg/kg |
| Example 2 | 56.49 mg/kg |
| Example 3 | 88.63 mg/kg |
| Comparative example 1 | $3.24 * 10^4$ mg/kg |
| Comparative example 2 | $1.52 * 10^5$ mg/kg |
| Comparative example 3 | $3.65 * 10^4$ mg/kg |

It can be concluded from the results of Table 1 that:

1. In the fish protein oligopeptide with low allergenicity and slight fishiness prepared by the present invention, mass content of the dominant allergenic protein, i.e., parvalbumin can be reduced by 99% or above, which is a significant effect. This suggested that the method of the present invention was able to completely eliminate the allergenicity of fish proteins, and had good allergenicity elimination effect.

2. Use of a neutral protease and bromelain for processing the fish proteins was capable of eliminating the allergenicity of fish proteins to a certain extent, but had a less-than-satisfactory allergenicity elimination effect. Use of a trypsin for processing the fish proteins had no obvious allergenicity elimination effect; on the contrary, it was detected that the allergenic parvalbumin had a slightly increased content.

This showed that: not arbitrary proteases or combinations thereof were able to reduce or eliminate the allergenicity of fish proteins when being used for processing the fish proteins, and only using proteases with specific composition and meanwhile using specific processes (for example, pH environment, temperature, etc., of the enzymolysis) were able to completely eliminate the allergenicity of the fish proteins.

TABLE 2

Molecular weight distribution of the fish protein oligopeptide with low allergenicity and slight fishiness

| Range of molecular weight | Example 1 | Example 2 | Example 3 |
| --- | --- | --- | --- |
| More than 5000 | 0.09 | 0.15 | 1.78 |
| 3000-5000 | 0.04 | 0.29 | 0.71 |
| 1000-3000 | 3.78 | 3.69 | 8.23 |
| 500-1000 | 16.59 | 14.21 | 21.82 |
| 140-500 | 73.57 | 64.70 | 60.49 |
| less than 140 | 5.82 | 16.79 | 6.83 |
| Ratio of molecular weight less than 1000 | 95.98 | 95.70 | 89.14 |
| Ratio of molecular weight less than 5000 | 99.80 | 99.67 | 98.07 |

It can be concluded from the results of Table 2 that:

In the fish protein oligopeptide with low allergenicity and slight fishiness prepared by the present invention, mass content of peptides with a molecular weight of less than 5000 Da is >85%, and mass content of peptides with a molecular weight of less than 1000 Da is >60%. Therefore, the fish protein oligopeptide with low allergenicity and slight fishiness of the present invention can be well absorbed by human body, and thus had high available protein content.

TABLE 3

Taste evaluation results of the fish protein oligopeptide with low allergenicity and slight fishiness

| Experimental examples | Average bitterness value | Fishiness value |
| --- | --- | --- |
| Example 1 | 2 | 1 |
| Example 2 | 3 | 2 |
| Example 3 | 2 | 2 |
| Comparative example 1 | 8 | 6 |
| Comparative example 2 | 7 | 6.5 |
| Comparative example 3 | 5 | 4 |

It can be concluded from the results of table 3 that:

The fish protein oligopeptide with low allergenicity and slight fishiness prepared by the present invention had a small bitterness and fishiness, and excellent taste, showing that the method of the present invention was able to effectively inhibit generation of bitterness substances in enzymolysis products, and significantly remove fishy substances in fish proteins; only using proteases for processing the fish proteins was unable to effectively prevent release of bitter components from the fish proteins as well as removal of the fishy substances, and only if using proteases with specific composition in combination with specific processes (for example, pre-denaturation and membrane filtration) can completely remove the fishiness and bitterness, and guarantees taste of fish products.

Finally it should be state that, the above embodiments are merely intent to illustrate rather than to limit the technical solutions of the present invention; and although the present invention has been detailed in conjunction with the above embodiments, one with ordinary skill in the art should understand that, modifications can still be made to the technical solutions recorded in the above embodiments, or that equivalent substitutions can still be made to part or all of the technical features; and neither these modifications nor these substitutions shall make essence of the corresponding technical solutions deviate from the range of the technical solutions in each example of the present invention.

What is claimed is:

1. An industrial method for preparation of a fish protein oligopeptide with low allergenicity and slight fishiness, comprising the following steps in order:
    a) washing fresh fish flesh and/or fish wastes, crushing, and adding water to obtain a mixture;
    b) performing thermal denaturation on the mixture to obtain a denaturized protein solution;
    c) pre-centrifuging the first denaturized protein solution to obtain a first precipitate, and adding water into the first precipitate and washing to obtain a second denaturized protein solution, wherein a mass to volume ratio of the first precipitate and the water is 1:1 to 1:5, centrifuging the second denaturized protein solution to obtain a second precipitate, and adding water into the second precipitate and grinding, to obtain a slurry;
    d) adjusting the slurry to pH 6-9, and sequentially adding a neutral protease, a papain and an alkaline protease to conduct enzymolysis, and after enzyme inactivation, to obtain an enzymatic hydrolysate;
    e) centrifuging the enzymatic hydrolysate to obtain a supernatant, and performing membrane filtration on the centrifuged supernatant of enzymatic hydrolysate, to obtain the fish protein oligopeptide with low allergenicity and slight fishiness.

2. The method in accordance with claim 1, wherein a mass to volume ratio of the fish flesh and/or fish wastes and the water in step a) is 1:1 to 1:5, and a mass to volume ratio of the precipitate and the water in step c) is 1:1 to 1:5.

3. The method in accordance with claim 1, wherein the thermal denaturation comprises: heating the mixture to 75-95° C., maintaining this temperature and continuously stirring for 10-60 min.

4. The method in accordance with claim 1, wherein an amount of the neutral protease is 10-100 U/g, an amount of the papain is 10-100 U/g, and an amount of the alkaline protease is 10-100 U/g.

5. The method in accordance with claim 4, wherein an amount ratio of the neutral protease, the papain and the alkaline protease is 1:1 to 1:3 to 1:3.

6. The method in accordance with claim 1, wherein the enzymolysis is carried out at 30° C.-60° C., and time of the enzymolysis is controlled to be 2-6 h.

7. The method in accordance with claim 1, wherein a filtration membrane with a pore diameter of 1-100 nm is used for the membrane filtration.

* * * * *